United States Patent
Shimada et al.

(10) Patent No.: US 12,109,479 B2
(45) Date of Patent: Oct. 8, 2024

(54) EXERCISE ASSISTANCE DEVICE, EXERCISE ASSISTANCE METHOD, AND STORAGE MEDIUM

(71) Applicant: CASIO COMPUTER CO., LTD., Tokyo (JP)

(72) Inventors: Keisuke Shimada, Hamura (JP); Takashi Yahata, Hamura (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 394 days.

(21) Appl. No.: 17/605,562

(22) PCT Filed: Feb. 19, 2020

(86) PCT No.: PCT/JP2020/006417
§ 371 (c)(1),
(2) Date: Oct. 21, 2021

(87) PCT Pub. No.: WO2020/217667
PCT Pub. Date: Oct. 29, 2020

(65) Prior Publication Data
US 2022/0203207 A1 Jun. 30, 2022

(30) Foreign Application Priority Data
Apr. 23, 2019 (JP) .................. 2019-082235

(51) Int. Cl.
*A63B 24/00* (2006.01)
*A63B 71/06* (2006.01)
*A63B 69/00* (2006.01)

(52) U.S. Cl.
CPC ...... *A63B 71/0622* (2013.01); *A63B 24/0062* (2013.01); *A63B 69/0028* (2013.01);
(Continued)

(58) Field of Classification Search
CPC ............ A63B 71/0622; A63B 24/0062; A63B 69/0028; A63B 2071/0663;
(Continued)

(56) References Cited

U.S. PATENT DOCUMENTS 10,499,833 B2 * 12/2019 Li ........................... A61B 5/11
2014/0288681 A1 9/2014 Watanabe
(Continued)

FOREIGN PATENT DOCUMENTS

JP H04105667 A 4/1992
JP 2013143996 A 7/2013
(Continued)

OTHER PUBLICATIONS

Laity, "Principal Component analysis: pictures, code and proofs", Oct. 2018 (Year: 2018).*
(Continued)

*Primary Examiner* — Robert R Raevis
(74) *Attorney, Agent, or Firm* — Holtz, Holtz & Volek PC

(57) ABSTRACT

An exercise assistance device includes a data obtainer that obtains motion data on a motion of an arm of a user that is taking exercise while swinging the arm, and at least one processor that obtains a type of arm swing form of the user, based on the motion data obtained by the data obtainer.

8 Claims, 11 Drawing Sheets

(52) U.S. Cl.
CPC ... *A63B 2071/0663* (2013.01); *A63B 2214/00* (2020.08); *A63B 2220/803* (2013.01); *G06F 2218/12* (2023.01)

(58) Field of Classification Search
CPC .......... A63B 2214/00; A63B 2220/803; G06F 2218/12; A61B 5/002; A61B 5/0022; A61B 5/1114; A61B 5/1121; A61B 5/1123; A61B 5/1126; A61B 2503/10; A61B 2505/09; A61B 2562/0219; A61B 2562/0223; A61B 5/681
USPC ......... 73/865.4; 702/33, 127, 141, 142, 145, 702/150–153, 167; 482/8, 14, 51, 54, 482/148; 438/8, 14, 51, 54, 148
See application file for complete search history.

(56) References Cited

U.S. PATENT DOCUMENTS

| | | |
|---|---|---|
| 2015/0120022 A1 | 4/2015 | Aoki et al. |
| 2015/0127126 A1 | 5/2015 | Yamagata et al. |
| 2018/0129275 A1 | 5/2018 | Isomura et al. |

FOREIGN PATENT DOCUMENTS

| | | | |
|---|---|---|---|
| JP | 2014180483 A | | 9/2014 |
| JP | 2015085030 A | | 5/2015 |
| JP | 2015109946 A | | 6/2015 |
| JP | 2018077606 A | | 5/2018 |
| KR | 20190035786 A | * | 4/2019 |

OTHER PUBLICATIONS

International Preliminary Report on Patentability (IPRP) (and English language translation thereof) dated Sep. 28, 2021, issued in International Application No. PCT/JP2020/006417.

Japanese Office Action (and English language translation thereof) dated Jul. 27, 2021 issued in Japanese Application No. 2019-082235.

Written Opinion dated Apr. 14, 2020 issued in International Application No. PCT/JP2020/006417.

International Search Report (ISR) (and English language translation thereof) dated Apr. 14, 2020 issued in International Application No. PCT/JP2020/006417.

\* cited by examiner

FIRST DIRECTION ⇩

SECOND DIRECTION ⇨

THIRD DIRECTION ⇖

EXERCISE ASSISTANCE DEVICE, EXERCISE ASSISTANCE METHOD, AND STORAGE MEDIUM

CROSS-REFERENCE TO RELATED APPLICATIONS

This application is based upon and claims the benefit of priority of Japanese Patent Application No. 2019-082235 filed on Apr. 23, 2019, the entire disclosure of which is incorporated herein by reference in its entirety.

TECHNICAL FIELD

The present invention relates to an exercise assistance device, an exercise assistance method, and a program.

BACKGROUND ART

There has been a growing number of people who perform daily exercise, such as running.

Each kind of exercise has its own proper form. In running, swinging arms in a proper form is considered especially important.

Arm swing in running is considered to have positive effects, such as: generating a tempo and a rhythm; balancing and stabilizing the body and restraining weight shift; and improving a stride (specifically, by swinging arms while paying attention to shoulder blades, the shoulder blades move and the pelvis moves forward along with the movement of the shoulder blades, which naturally widens a stride).

Therefore, maintaining a proper form of arm swing is important in running.

However, a user may find it difficult to autonomously recognize the state of motions in exercise.

Further, even though the user considers he/she is aware of the form, the form may unconsciously break down owing to fatigue, for example.

In this regard, JP2014-180483A discloses a technology with a detector that detects motion data regarding the state of motion in exercise. According to the technology, the state of motion in exercise, such as how much the arms are swung, is obtained and provided for the user as exercise assistance information.

SUMMARY OF INVENTION

Solution to Problem

An exercise assistance device according to the present invention includes: a data obtainer that obtains motion data on a motion of an arm of a user that is taking exercise while swinging the arm; and an arm-swing type obtainer that obtains a type of arm swing form of the user, based on the motion data obtained by the data obtainer.

DESCRIPTION OF EMBODIMENTS

Hereinafter, an embodiment of an exercise assistance device according to the present invention is described in detail with reference to the drawings. In this embodiment, the description refers to a case where a user does walking or running.

<Configuration of Exercise Assistance Device>

Figure 1:
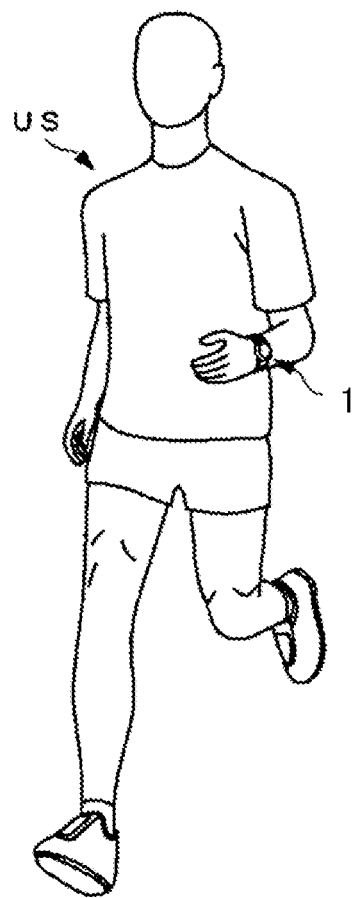
FIG. 1 is a schematic configuration of an exercise assistance device in a state of being used in an embodiment.

FIG. 1 is a schematic configuration of the exercise assistance device in a state of being used in this embodiment.

Figure 2:
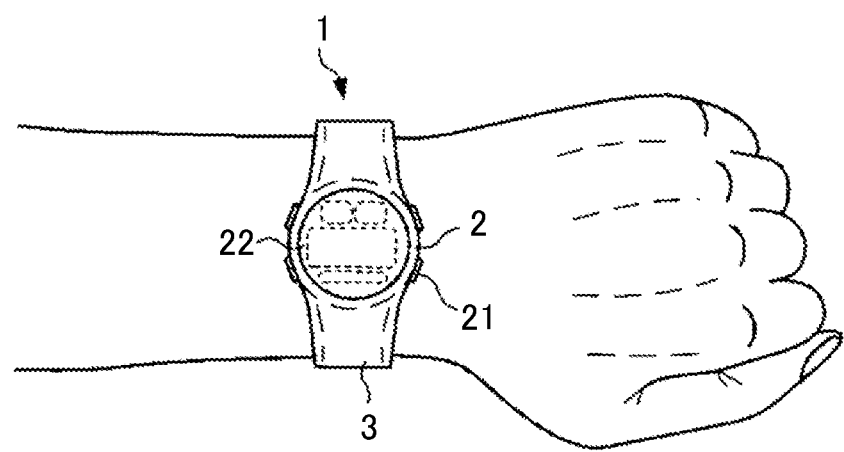
FIG. 2 is an external appearance of main parts of the exercise assistance device in the embodiment.

FIG. 2 is a main functional diagram showing an external appearance of the exercise assistance device in this embodiment.

As shown in FIG. 1 and FIG. 2, the exercise assistance device 1 in this embodiment is configured in a form of wristwatch and worn on the front arm (wrist) of a user US for use.

As shown in FIG. 2, the exercise assistance device 1 includes a device body 2 and a belt 3. The belt 3 is wound round the front arm (wrist) of the user US so that the device body 2 is worn by the user US.

The device body 2 of the exercise assistance device 1 is provided with an operation button 21 that constitutes an operation receiver 14 (see FIG. 3), which is described later.

The operation button 21 is provided on the lateral side of the device body 2, for example. When the user performs an operation of pressing or rotating the operation button 21, the operation button 21 outputs an operation signal corresponding to the operation to an arithmetic circuit 100, which is described later.

The display 22 is provided on the visible side of the device body 2 and displays various kinds of character information and image information.

The display 22 has a display panel that is a liquid crystal type capable of performing color display and monochrome display or a light-emitting type using organic electro-luminescence elements, for example.

The contents to be displayed on the display 22 is not limited to specific contents. The display 22 may display current time like a normal watch. The display 22 may also display various kinds of information, such as the time elapsed after the start of running, the running speed, and the lap time.

Further, the display 22 may display motion data (also called sensor data) obtained by various sensors, information on the type of arm-swing form of the user US obtained on the basis of the motion data (hereinafter called arm-swing type information), and other kinds of information. The various sensors are, for example, an acceleration sensor 11, an angular speed sensor 12, and a geomagnetic sensor 13 (see FIG. 3).

The contents displayed on the display 22 may be switched according to operations made on the operation button 21, for example. The user US may be able to do post facto setting for customizing what information items are displayed and how the information items are arranged. The display 22 may display one information item on the whole display region. Alternatively, the display region may be divided into multiple display areas on the basis of setting, for example, so that multiple information items are displayed next to each other simultaneously.

The display 22 may be integrated with a touchscreen. In such a case, the display 22, which serves as a touchscreen, may be able to receive various settings and input operations. In the case, the input receiver 14 includes the touchscreen of the display 22.

Figure 3:
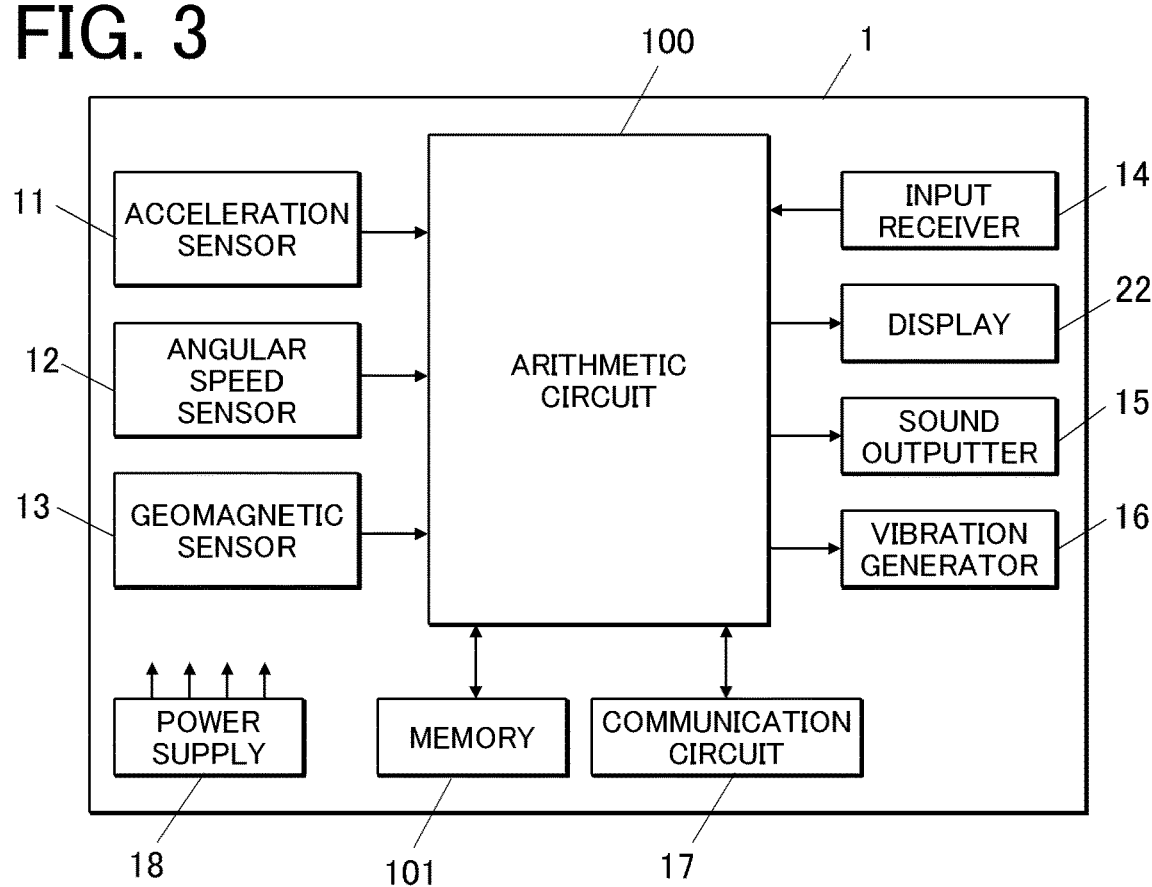
FIG. 3 is a functional block diagram showing an example of configuration of the exercise assistance device in the embodiment.

FIG. 3 is a block diagram showing an example of configuration of the exercise assistance device in this embodiment.

As shown in FIG. 3, the exercise assistance device 1 is provided with various sensors that obtain various kinds of data related to the user US who is wearing the exercise assistance device 1.

In this embodiment, these sensors are data obtainers that obtain motion data on the motion of the arm of the user when the user is taking exercise while swinging the arm.

The exercise assistance device 1 to be described in this embodiment includes the acceleration sensor 11, the angular speed sensor 12, and the geomagnetic sensor 13.

The acceleration sensor 11 includes a triaxial acceleration sensor, for example. The acceleration sensor 11 detects acceleration in each axis that the exercise assistance device 1 undergoes while the user US is taking exercise. The acceleration sensor 11 outputs the acceleration data (three-dimensional acceleration vector data) as motion data (sensor data).

The acceleration data output by the acceleration sensor 11 is signal components in three axis directions (X axis, Y axis, and Z axis) that cross each other at right angles.

Figure 4:
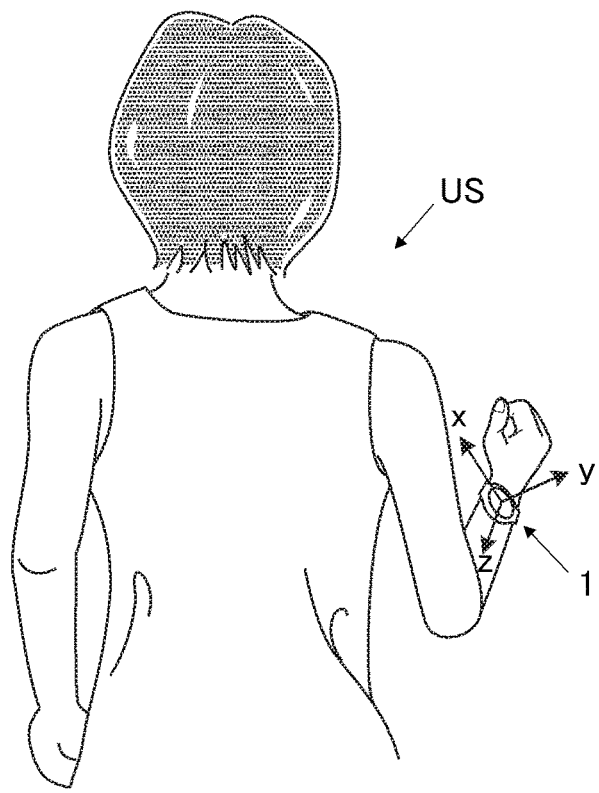
FIG. 4 is an illustration to explain three axis directions of the exercise assistance device in the state of being used.

FIG. 4 is an illustration to explain three axis directions when the exercise assistance device is used.

The three axes of the acceleration sensor 11 are: the Y axis in the direction perpendicular to the back of the hand of the user US taking exercise; the X axis in the direction parallel to the back of the hand and perpendicular to the Y axis; and the Z axis in the direction perpendicular to the X and Y axes (direction along the arm), as shown in FIG. 4, for example.

The acceleration data in the three axes is combined by the arithmetic circuit 100 (described later), associated with time data, and stored as time series data in a predetermined storage area of the memory 101.

The angular speed sensor 12 includes a triaxial angular speed sensor, for example. The angular speed sensor 12 detects the angular speed in each axis that the exercise assistance device 1 undergoes while the user US is taking exercise. The angular speed sensor 12 outputs the angular speed data (three-dimensional angular speed vector data) as motion data (sensor data). The angular speed data output by the angular speed sensor 12 is output as signal components in three axes (X axis, Y axis, and Z axis) that cross each other at right angles. The three axis directions (X axis, Y axis, and Z axis) are the same as those of the acceleration sensor 11 shown in FIG. 4. The angular speed data in the three axis directions is combined by the arithmetic circuit 100 (described later), associated with time data, and stored as time series data in a predetermined storage area of the memory 101.

The geomagnetic sensor 13 is a triaxial geomagnetic sensor, for example. The geomagnetic sensor 13 detects the geomagnetism in each axis that the exercise assistance device 1 undergoes while the user US is taking exercise. The geomagnetic sensor 13 outputs the geomagnetic data (three-dimensional geomagnetic vector data) as motion data (sensor data). The geomagnetic data output by the geomagnetic sensor 13 are signal components in three axis directions (X axis, Y axis, and Z axis) that cross each other at right angles. The directions of three axes (X axis, Y axis, and Z axis) are the same as those of the acceleration sensor 11 and the angular speed sensor 12 shown in FIG. 4. The geomagnetic data in the three axis directions is combined by the arithmetic circuit 100 (described later), associated with time data, and stored as time series data in a predetermined storage area of the memory 101. The geomagnetic sensor 13 is operable with a relatively small power. The geomagnetic sensor 13 therefore contributes to reducing power requirements of the entire device when the geomagnetic sensor 13 is used instead of the other sensors.

When the exercise assistance device 1 includes multiple sensors, such as the acceleration sensor 11, the angular speed sensor 12, and the geomagnetic sensor 13 as in this embodiment, the motion data items (sensor data) obtained by the respective sensors may be used separately, or multiple motion data items (sensor data) obtained by multiple sensors may be used together so as to complement each other.

When data of a single sensor may not yield an accurate detection result for some reason, use of the motion data (sensor data) of multiple sensors can yield a more correct and accurate detection result.

The input receiver 14 receives various input operations by the user US and so forth.

The input receiver 14 includes input means, such as the abovementioned operation button 21, a touchscreen in a case where the touchscreen is integrated with the display 22, and a keyboard connected to the device body 2 via a wired or wireless connection.

The input receiver 14 is used for input operations, such as: controlling on/off of the sensing operations (measuring operation) of the above-described acceleration sensor 11, the angular speed sensor 12, and the geomagnetic sensor 13; inputting evaluations of the arm-swing state to be described later; and setting various items displayed on the display 22. The input receiver 14 may have one or more input means among the input means including the operation switch, the touchscreen, and the keyboard. When the input receiver 14 has multiple input means, these input means may perform the same or similar function, or may perform functions specific to the respective input means.

The sound outputter 15 has a sound outputting device, such as a buzzer and/or a speaker. The sound outputter 15 generates sound information, such as specific sounds, sound patterns (alarm), and voice messages. The sound outputter 15 thus aurally provides (notifies) the user US with information (exercise assistance information) that indicates the type of arm-swing form of the user US in the exercise assistance method.

The vibration generator 16 has a vibrator, such as a vibration motor or an oscillator. The vibration generator 16 generates vibration information, such as predetermined vibration patterns and its vibration strength. The vibration generator 16 thus tactically provides (notifies) the user US with information (exercise assistance information) that indicates the type of arm-swing form of the user US in the exercise assistance method.

The communication circuit 17 serves as an interface for sending, to an external device or the like, the sensor data (raw data) obtained by the acceleration sensor 11, the angular speed sensor 12, and the geomagnetic sensor 13 and arm-swing type information (exercise assistance information) generated on the basis of the sensor data.

Herein, the method of sending and receiving the exercise assistance information to and from the external device via the communication circuit 17 may be, for example, any wireless communication method or wired communication method via a communication cable.

In sending and receiving the exercise assistance information over a wireless communication, the Bluetooth (registered trademark), which is the near field communication standard for digital devices, may be appropriately used, for example. With such a wireless communication method, the communication circuit 17 can appropriately transmit data even when the power supply 18 (described later) generates low power using energy harvesting, for example.

The power supply 18 supplies driving power to the respective components in the device body 2 of the exercise assistance device 1. As the power supply 18, a commercially-available primary battery or a secondary battery may be used. The primary battery is, for example, a coin type battery or a button type battery. The secondary battery is, for example, a lithium-ion battery or a nickel-metal hydride battery. As the power supply 18, power supplies other than these primary and secondary batteries may be used, for example a power supply that generates power by utilizing vibration, light, heat, electromagnetic waves, and so forth (energy harvest technology).

The memory 101 has a data memory, a program memory, and a working memory in a rough classification.

The data memory has a nonvolatile memory, such as a flash memory. In a predetermined storage area of the data memory, sensor data (motion data) obtained by the acceleration sensor 11, the angular speed sensor 12, and the geomagnetic sensor 13 is associated with time data and stored as time series data.

Further, in a predetermined storage area of the data memory, arm-swing type information (exercise assistance information) is stored. The arm-swing type information is obtained on the basis of the motion data (sensor data) in the exercise assistance method, which is described later.

The program memory has a read only memory (ROM) and stores a control program for performing predetermined operations at the respective components. The predetermined operations are, for example, the sensing operation by the acceleration sensor 11, the angular speed sensor 12, and the geomagnetic sensor 13, and the display operation by the display 22 for displaying various kinds of information.

The program memory also stores an algorithm program for obtaining the type of arm-swing form of the user US and providing the type as the exercise assistance information.

The working memory has a random access memory (RAM). The working memory temporarily stores various kinds of data used or generated in executing the control program and the algorithm program.

The entire memory 101 or part of the memory 101 may be a removable storage medium, such as a memory card, so as to be attachable to and detachable from the device body 1 of the exercise assistance device 1.

The arithmetic circuit 100 is a processor that has the time keeping function, such as a central processing unit (CPU) or a micro processing unit (MPU). On the basis of a predetermined operation clock, the arithmetic circuit 100 executes the predetermined control program stored in the memory 101 (program memory). The arithmetic circuit 100 thus controls various operations, such as: the sensing operation of the acceleration sensor 11, the angular speed sensor 12, and the geomagnetic sensor 13; and the information display operation of the display 22.

The arithmetic circuit 100 in this embodiment further serves as an arm-swing type obtainer that obtains the type of arm-swing form of the user US on the basis of the motion data (sensor data) obtained by the acceleration sensor 11, the angular speed sensor 12, and the geomagnetic sensor 13. More specifically, the arithmetic circuit 100 as the arm-swing type obtainer performs the principal component analysis of the motion data obtained by the various sensors and, on the basis of the level of dispersion in the respective axis directions, obtains an indicator of the type of arm-swing form of the user US.

The arithmetic circuit 100 executes the predetermined algorithm program stored in the memory 101 (program memory) on the basis of the operation clock. The arithmetic circuit 100 thereby performs a series of exercise assistance processing in which the type of arm-swing form of the user US is obtained and the arm-swing type information is provided as the exercise assistance information. The detailed processing performed by the arithmetic circuit 100 is described later.

The control program and the algorithm program to be executed by the arithmetic circuit 100 may be installed beforehand in the arithmetic circuit 100.

<Exercise Assistance Method>

Next, the exercise assistance method in this embodiment is described. The exercise assistance method described herein is for a case where the user US does running as exercise.

Figure 5:
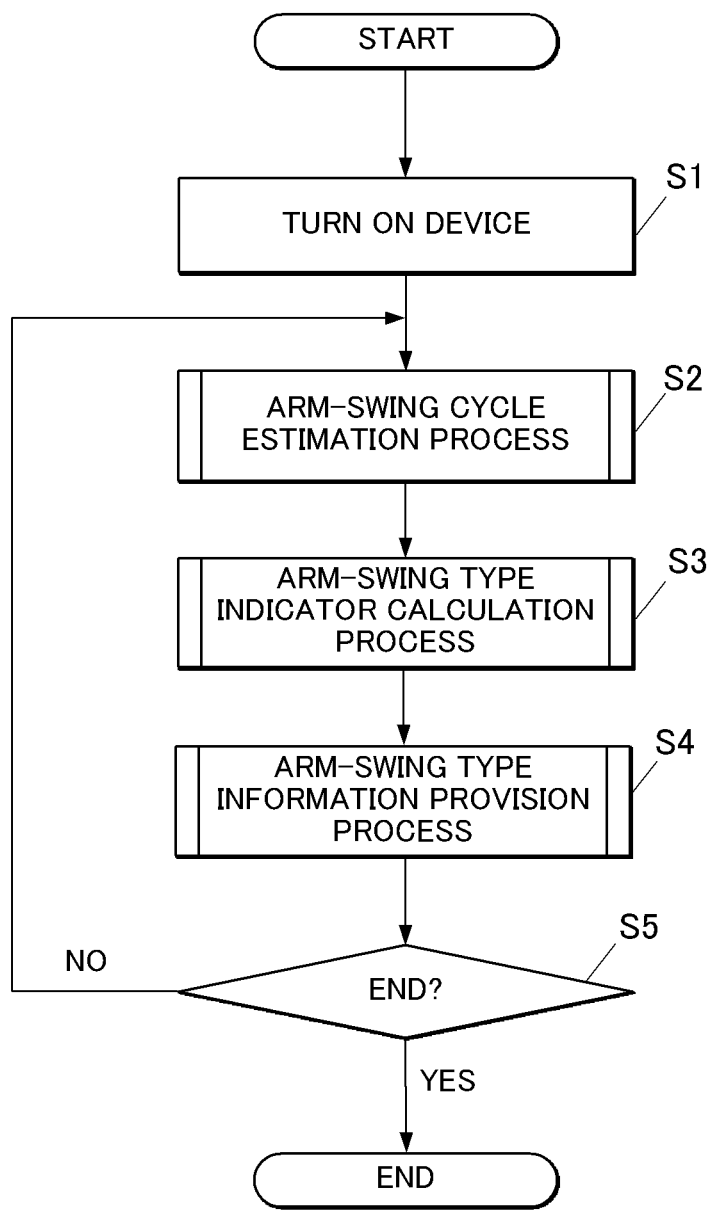
FIG. 5 is a flowchart showing an example of entire process flow of an exercise assistance method in the embodiment.

FIG. 5 is a flowchart showing an example of entire flow of the exercise assistance method by the exercise assistance device in this embodiment.

As shown in FIG. 5, a series of exercise assistance processes starts when the exercise assistance device 1 is turned on (Step S1). In the exercise assistance method in this embodiment, the exercise assistance processes are roughly classified into an arm-swing cycle estimation process (Step S2), an arm-swing type indicator calculation process (Step S3), and an arm-swing type information provision process (Step S4). These processes are performed successively. The exercise assistance device 1 continually determines whether the user US ends exercise (Step S5). When, for example, the exercise assistance device 1 is turned off or a predetermined time elapses without any operation or action, the exercise assistance device 1 determines that the exercise has ended (Step S5: YES) and ends the series of processes. When determining that the exercise has not ended yet (Step S5: No), the exercise assistance device 1 returns to Step 2 and repeats the process.

(Arm-Swing Cycle Estimation Process)

Figure 6:
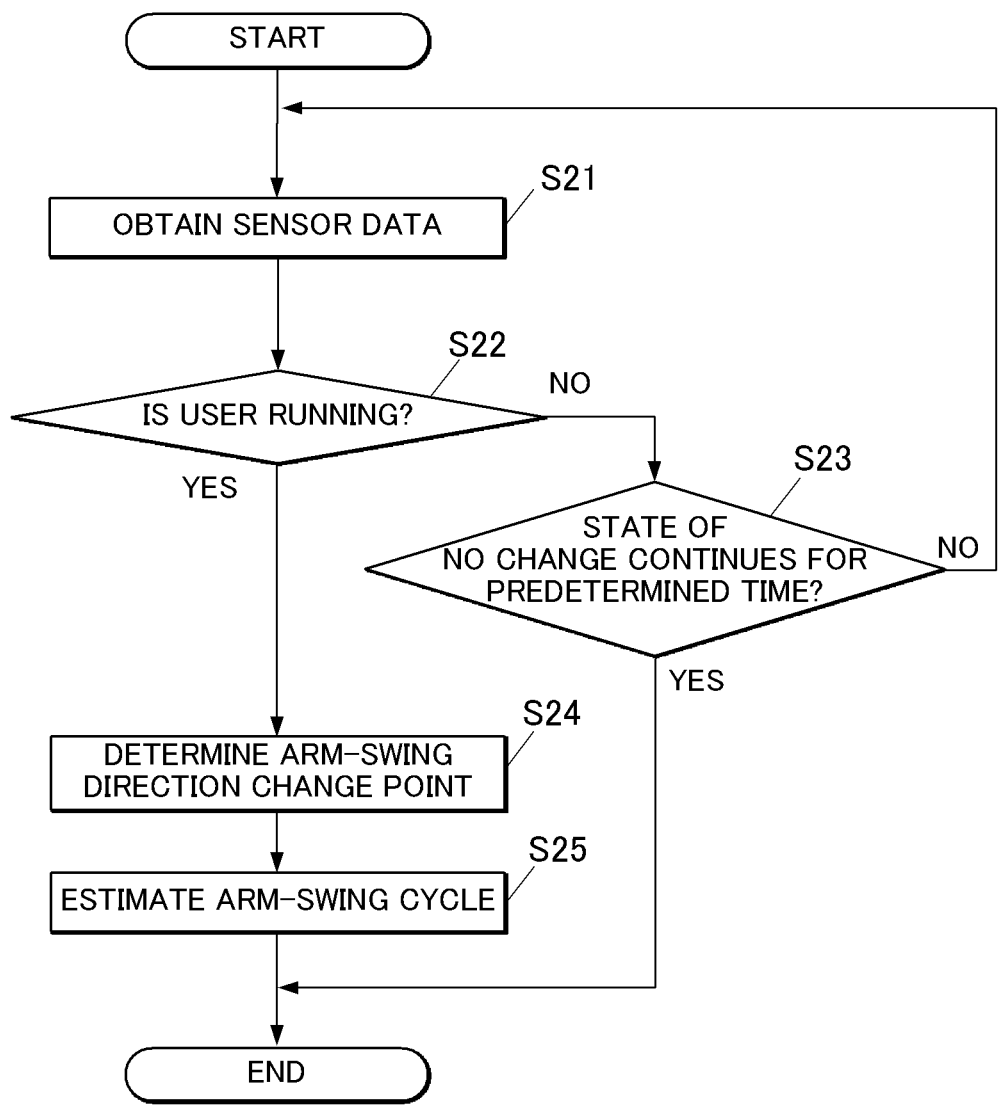
FIG. 6 is a flowchart showing an example of an arm-swing cycle estimation process in the embodiment.

FIG. 6 is an example of a flowchart of the arm-swing cycle estimation process as Step S2 in FIG. 5.

In analyzing the type of arm-swing form of the user taking exercise, the exercise assistance device 1 performs the process using motion data that corresponds to multiple cycles of arm swing in order to reduce effects of variation of the results. As a premise of the above, the cycle of the arm swing motion of the user US needs to be estimated. The arm-swing cycle estimation process is for estimating one cycle of the arm swing motion of the user US.

First, the arithmetic circuit 100 obtains motion data (sensor data) from the sensor(s) (Step S21). The motion data of any sensor among the sensors may be used. For example, the arithmetic circuit 100 obtains the motion data (acceleration data) obtained by the acceleration sensor 11.

On the basis of the obtained motion data, the arithmetic circuit 100 determines whether the user US is running (Step S22).

The method of determining whether the user US is running may be any method.

For example, the arithmetic circuit 100 determines whether the user US is running on the basis of whether the signal waveform of the resultant acceleration (motion data obtained by the acceleration sensor 11) has a specific waveform.

It is known that the signal waveform of the resultant acceleration during running shows a characteristic change in its cycle and strength, for example. By observing the acceleration data in three axis directions and/or the signal waveform of the resultant acceleration, the exercise assistance device 1 can accurately determine whether the user US is running or not.

When the signal waveform of the resultant acceleration does not show a specific waveform, the arithmetic circuit 100 determines that the user US is not running (Step S22: No). The arithmetic circuit 100 determines whether the state where the signal waveform does not show a specific waveform has continued for a predetermined period of time (Step S23). When determining that the state where the signal waveform of the resultant acceleration does not show a specific waveform has continued for a predetermined period of time (Step S23: Yes), the arithmetic circuit 100 ends the process. When determining that the state where the signal waveform of the resultant acceleration does not show a specific waveform has not continued for a predetermined period of time yet (Step S23: No), the exercise assistance device 1 returns to Step S21 and repeats the process.

On the other hand, when determining that the user US is running (Step S22: Yes), or more specifically, determining that the signal waveform of the resultant acceleration shows a specific waveform, the arithmetic circuit 100 determines a point of time at which the arm swing direction changes (Step S24).

The method of determining the point of time at which the arm swing direction changes is not limited to a specific method. For example, the arithmetic circuit 100 obtains the motion data obtained by the angular speed sensor 12 or the resultant angular speed data into which the motion data is combined, and determines the point of time at which the motion data reaches the minimum to be the point P (see FIG. 8) at which the arm swing direction changes.

Figure 7A:
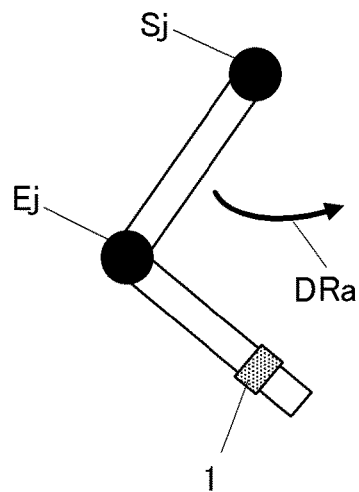
FIG. 7A is a schematic illustration showing an example of arm swing motion in which the arm is pulled backward.

The arm swing motion is a series of repetitive motions in which: the arm fully pulled backward (FIG. 7A) is swung forward (direction DRa in FIG. 7A); after being fully swung forward (FIG. 7B), the arm is pulled backward (direction DRb in FIG. 7B); and the arm returns to the state shown in FIG. 7A.

Figure 7B:
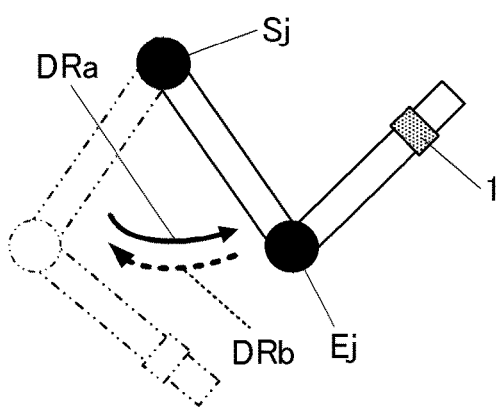
FIG. 7B is a schematic illustration showing an example of arm swing motion in which the arm is swung forward.

FIG. 7A and FIG. 7B schematically illustrate how the arm is swung back and forth. In FIG. 7A and FIG. 7B, the position of the shoulder joint is Sj, and the position of the elbow joint is Ej.

Figure 8:
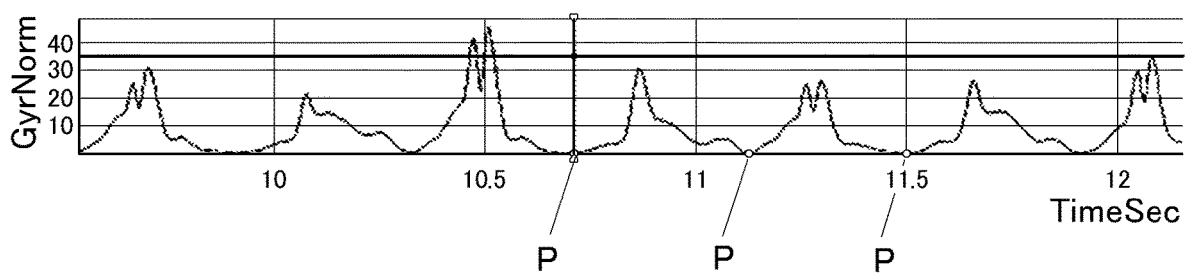
FIG. 8 is a signal waveform chart showing an example of sensor data that is obtained for estimating the arm swing cycle in the embodiment.

FIG. 8 is a signal waveform chart showing an example of sensor data that is obtained for estimating the arm swing cycle. In this embodiment, the motion data in each of three axis directions (X axis, Y axis, and Z axis) obtained by the angular speed sensor 12 is squared, and the squared results are added ($X^2+Y^2+Z^2$) to obtain the resultant angular speed data. FIG. 8 shows this resultant angular speed data plotted along the time series.

In FIG. 8, the timings (points of time) at which the angular speed (resultant angular speed) reaches the minimum correspond to: the state where the arm is fully pulled backward (i.e., the state shown in FIG. 7A); the state where the arm is fully swung forward (i.e., the state shown in FIG. 7B) from the state shown in FIG. 7A; and the state where the arm is again fully pulled backward. At these points of time, the arm swing direction changes.

The arithmetic circuit 100 determines that the timings (point of time, time) at which the angular speed (resultant angular speed) reaches the minimum is the points P at which the arm swing direction changes, and stores the points P in the memory 101.

One cycle of the arm swing motion is one time of arm swing from the back to the front and from the front to the back. The arithmetic circuit 100 determines the points P at which the arm swing direction changes by using the resultant angular speed data of the angular speed sensor 12, for example. Thus, the arithmetic circuit 100 can accurately estimate one cycle of the arm swing motion of the user US (Step S25).

Assume that motion data corresponding to 10 cycles of the arm swing motion is used for calculating the arm-swing type indicator, for example. In such a case, the arithmetic circuit 100 can easily determine the range of motion data to be used for the calculation process by estimating the cycle of arm swing motion of the user.

The range of the motion data to be used for the calculation process may be determined on the basis of a predetermined period of time, instead of the number of cycles of the arm swing motion. After the cycle of arm swing motion of the user US is estimated, the time required for one cycle is multiplied by 10, and the motion data corresponding to the multiplied time range is used. This yields the same result as in the case where the motion data corresponding to 10 cycles is used. Alternatively, the range of the motion data to be used for the calculation process can be determined on the basis of distances.

The arm-swing cycle estimation process is a preprocess for the following arm-swing type indicator calculation process, which uses the motion data corresponding to multiple cycles of arm swing motion. The detailed method for the arm-swing cycle estimation process is therefore not limited to the method exemplified herein, and can be any other appropriate method.

For example, the arm swing motion substantially synchronizes with paces of feet. The exercise assistance device 1 may be provided with a sensor capable of obtaining the paces of feet (i.e., distance or time in which one foot contacts the ground, leaves the ground, and again contacts the ground). The motion data (sensor data) obtained by such a sensor may be used for estimating the arm swing cycle. The method of obtaining the paces of feet may be, for example, a method of obtaining the motion data from an acceleration sensor attached to the foot/leg or the waist. In the method, the exercise assistance device 1 attached to the arm and the acceleration sensor attached to the foot/leg/waist cooperate by communicating with each other, for example.

Further, a precise arm swing cycle may not be obtained. The exercise assistance device 1 can refer to a typical time or distance required for one cycle of arm swing, multiply the cycle by a predetermined number (e.g., 10), and analyze the motion data corresponding to the predetermined number of cycles (e.g., 10 cycles) of arm swing motion.

(Arm-swing type indicator calculation process)

Next, the arm-swing type indicator calculation process in this embodiment is described.

Figure 9:
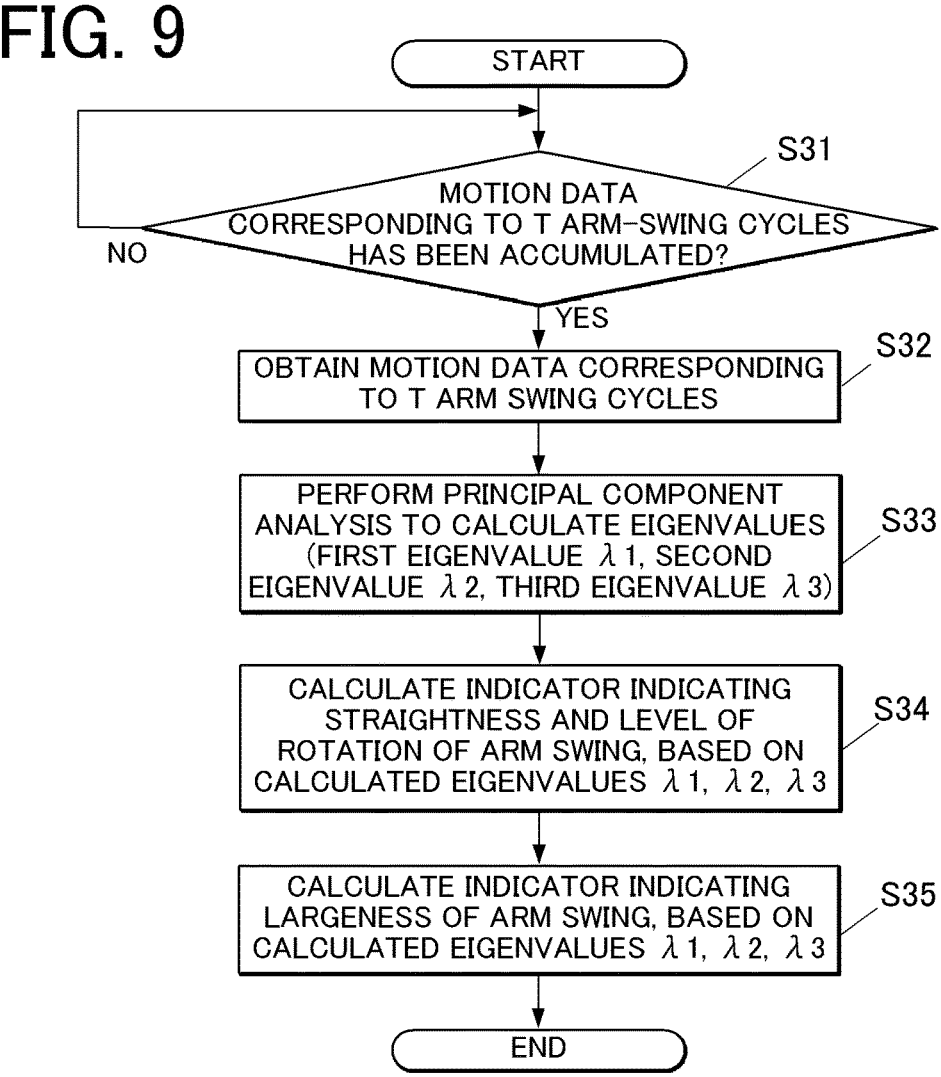
FIG. 9 is a flowchart showing an example of an arm-swing type indicator calculation process in the embodiment.

FIG. 9 is a flowchart showing an example of the arm-swing type indicator calculation process as Step S3 in FIG. 5.

In the arm-swing type indicator calculation process, the arithmetic circuit 100 firstly determines whether the motion data (sensor data) corresponding to T cycles of arm swing motion has been accumulated (Step S31).

The specific number of "T cycles" depends on usages and conditions.

For example, in order to know the type of arm-swing form in a long term, it is preferable to analyze the arm-swing form during the long term on the basis of the motion data for a greater number of cycles. In order to know the type of arm-swing form in a short term, it is preferable to analyze the arm-swing form during the short term on the basis of the motion data for a smaller number of cycles.

Herein, the long term refers to a period ranging from a few minutes to 10 minutes or so, for example. The short term refers to seven or eight cycles, for example.

The motion data for a small number of cycles (e.g., one cycle) may not yield an accurate result owing to variation, as mentioned above.

On the other hand, the type of arm-swing form changes depending on various conditions, such as: the running speed; the degree of fatigue (e.g., the degree of fatigue accumulated as the time elapses after the start of running); and the state of the running road (e.g., on-road running, off-road running, the percentage of the incline of the running road). Therefore, processing the entire motion data for a day's running may not yield an accurate meaningful result because the characteristics are averaged.

Assume that a large amount of motion data is obtained (e.g., running data of one day) and that the arm-swing type indicator calculation process is performed one time at the end of running/training for the day. In such a case, it is preferable that: the motion data to be processed be divided and subjected to the calculation process multiple times; and the process result be stored in association with the time at which the motion data, which was used in the process, was obtained.

Accordingly, changes in types of the arm swing form during the day can be chronologically checked (e.g., about what time and how the form broke down). This can give a meaningful process result to the user.

When the amount of data to be processed is large, the motion data may be appropriately thinned out for the process. This reduces burdens on the arithmetic circuit 100 and the memory 101, and also contributes to power saving.

When determining that the motion data corresponding to a predetermined number of cycles has not been accumulated (Step S31: No), the arithmetic circuit 100 repeats this determination process until the motion data is accumulated.

When determining that the motion data for a predetermined number of cycles has been accumulated (Step S31: Yes), the arithmetic circuit 100 obtains the motion data (sensor data) corresponding to T cycles of the arm swing motion from the memory 101 (Step S32). The arithmetic circuit 100 performs the principal component analysis of the obtained motion data to calculate the first eigenvalue $\lambda 1$ for the first axis, the second eigenvalue $\lambda 2$ for the second axis, and the third eigenvalue $\lambda 3$ for the third axis (Step S33).

In this embodiment, the arithmetic circuit 100 projects the angular speed data obtained by the triaxial angular speed sensor 12 in a three-dimensional space, performs the principal component analysis in the space, and calculates the eigenvalues ($\lambda 1$, $\lambda 2$, $\lambda 3$) for the respective axes.

On the basis of the eigenvalues ($\lambda 1$, $\lambda 2$, $\lambda 3$) for the respective axes calculated in Step S33, the arithmetic circuit 100 calculates indicators (arm-swing type indicators) indicating the type of arm-swing form. In this embodiment, the arithmetic circuit 100 calculates two indicators indicating the type of the arm swing form (arm-swing type indicators). One is the indicator indicating the straightness and the level of rotation of the arm swing motion, and the other is the indicator indicating the largeness of the arm swing motion.

The indicators calculated by the arithmetic circuit 100 are not limited to these two indicators. Any other indicator indicating the type of arm-swing form (arm-swing type indicator) may be calculated, or only either of the two indicators may be calculated.

In the description below, the arithmetic circuit 100 calculates the indicator indicating the straightness and the level of rotation of the arm swing motion and then calculates the indicator indicating the largeness of the arm-swing motion. However, the order of calculation of these indicators is not limited to the example shown in the description.

First, the arithmetic circuit 100 calculates the indicator indicating the straightness and the level of rotation of the arm-swing motion as the indicator indicating the type of arm-swing form (arm-swing type indicator) (Step S34).

The calculation result of the arithmetic circuit 100 is appropriately stored in the memory 101.

More specifically, the following expression is used.

$$\text{LR\_Coeff} = \lambda 2/\lambda 1 + \alpha \lambda 3/\lambda 1 + \beta \lambda 3/\lambda 2 \qquad \text{Expression 1}$$

Herein, α=1 and β=0, for example.

When LR_Coeff≤0.1 stands, the user is determined as the type of a higher straightness (straight type, plane-surface type).

When LR_Coerr≥0.3 stands, the user is determined as the type of a higher level of rotation (rotative type, curve type).

The type of a higher straightness (straight type, plane-surface type) refers to a type of arm-swing form in which the arm is moved back and forth relatively linearly. The type of a higher level of rotation (rotative type, curve type) is a type of arm-swing form in which the user swings the arm in circular motions.

Types of arm-swing form are not limited to these two types only (straight type and rotative type).

For example, the indicator indicating the straightness and the indicator indicating the level of rotation may be shown in percentage (%), and intermediate/phased evaluations may be presented as indicators (e.g., evaluation of which type the user is closer).

Further, the result of the principal component analysis itself may be presented as an indicator indicating the type of arm-swing form of the user US.

The expression for calculating the arm-swing type indicator is not limited to the above expression 1.

For example, it is not essential to use the coefficients α, β. Only either of the coefficients may be used, or none of the coefficients may be used.

Further, it is not necessary to consider all of the items "$\lambda 2/\lambda 1$", "$\lambda 3/\lambda 1$", and "$\lambda 3/\lambda 2$". For example, when rather simple calculation is enough, only the item "$\lambda 2/\lambda 1$" may be used for simple calculation.

Next, on the basis of the eigenvalues ($\lambda 1$, $\lambda 2$, $\lambda 3$) for the respective axes calculated in Step S33, the arithmetic circuit 100 calculates an indicator indicating the largeness of arm-swing motion as an indicator indicating the type of arm-swing form (arm-swing type indicator) (Step S35). The order of Step S34 and Step S35 is not specifically determined.

On the basis of the motion data obtained by the sensor(s), the arithmetic circuit 100 performs the principal component analysis to see how much the data is dispersed in each axis. By doing this, the arithmetic circuit 100 can calculate how largely the user US swings the arm (largeness of the arm swing motion).

The calculation result of the arithmetic circuit 100 is appropriately stored in the memory 101.

More specifically, the arithmetic circuit 100 calculates the largeness of the arm-swing motion by using the following expression.

$$\text{Size\_Coeff} = \lambda 1^2 + \lambda 2^2 + \lambda 3^2 \qquad \text{Expression 2}$$

The expression for calculating the arm-swing type indicator of the largeness of arm-swing motion is not limited to the above expression 2.

For example, it is not essential to square the eigenvalues for the respective axes ($\lambda 1$, $\lambda 2$, $\lambda 3$).

FIG. 10A to FIG. 10D and FIG. 11A to FIG. 11D show examples of plots of the result of the principal component analysis of the triaxial angular speed data, which is obtained by the angular speed sensor 12.

Figure 10A:
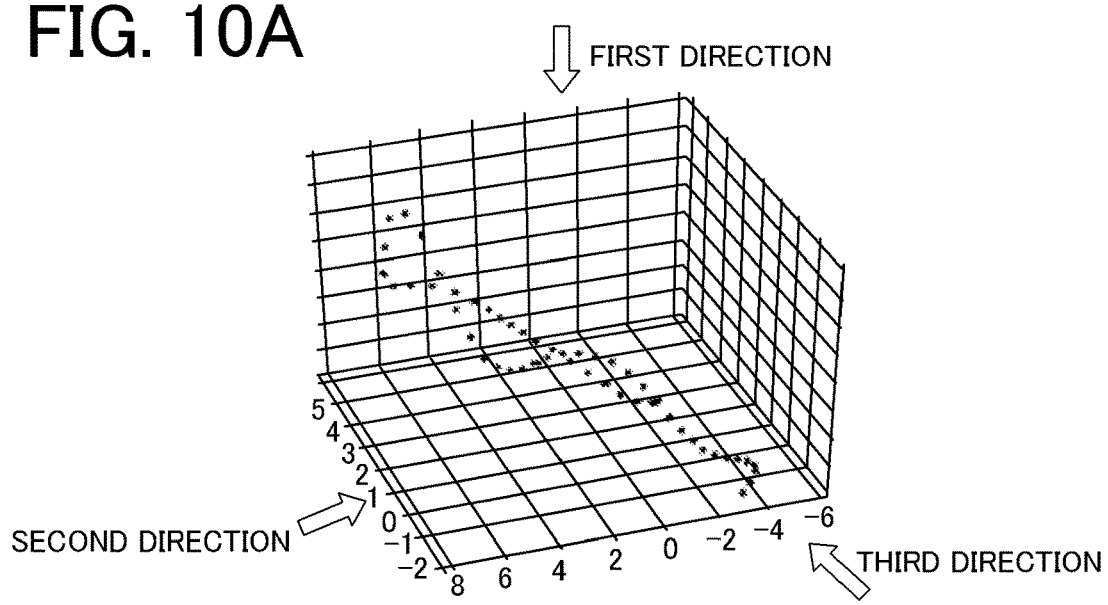
FIG. 10A is a graph showing an example of plotting the detection result of a straight-type arm-swing form, the result being obtained by an angular speed sensor.
Figure 10B:
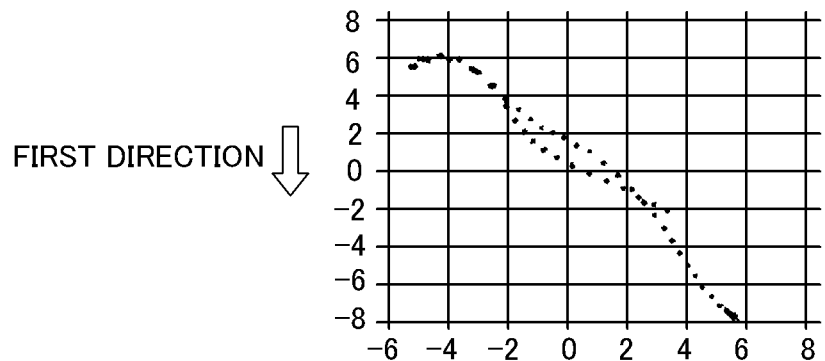
FIG. 10B is a graph showing an example of plotting the detection result of the straight-type arm-swing, the result being obtained by the angular speed sensor.
Figure 10C:
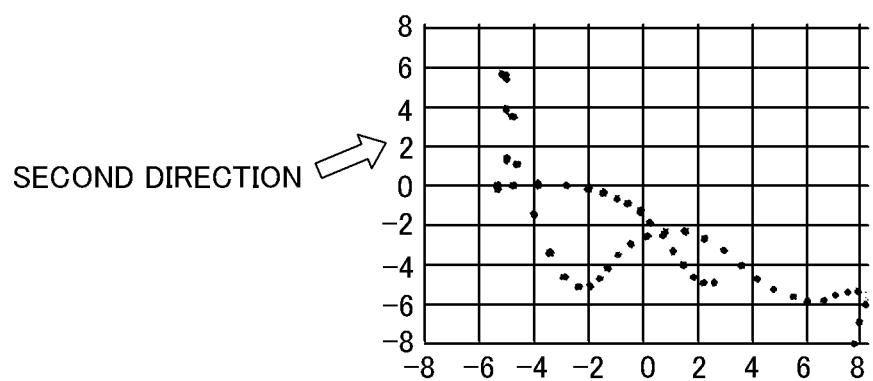
FIG. 10C is a graph showing an example of plotting the detection result of the straight-type arm-swing form, the result being obtained by the angular speed sensor.
Figure 10D:
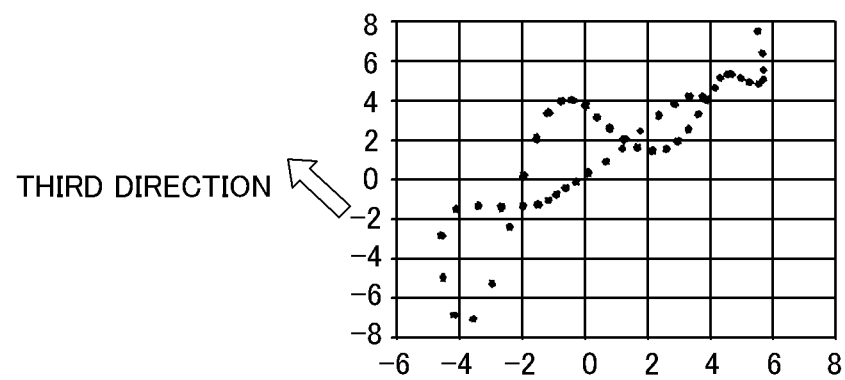
FIG. 10D is a graph showing an example of plotting the detection result of the straight-type arm-swing form, the result being obtained by the angular speed sensor.

FIG. 10B to FIG. 10D show how much the data disperses (is distributed) in the respective axes when seen from the directions in FIG. 10A (first direction, second direction, third direction in FIG. 10A). FIG. 10B shows the data seen from the first direction. FIG. 10C shows the data seen from the second direction. FIG. 10D shows the data seen from the third direction.

Figure 11A:
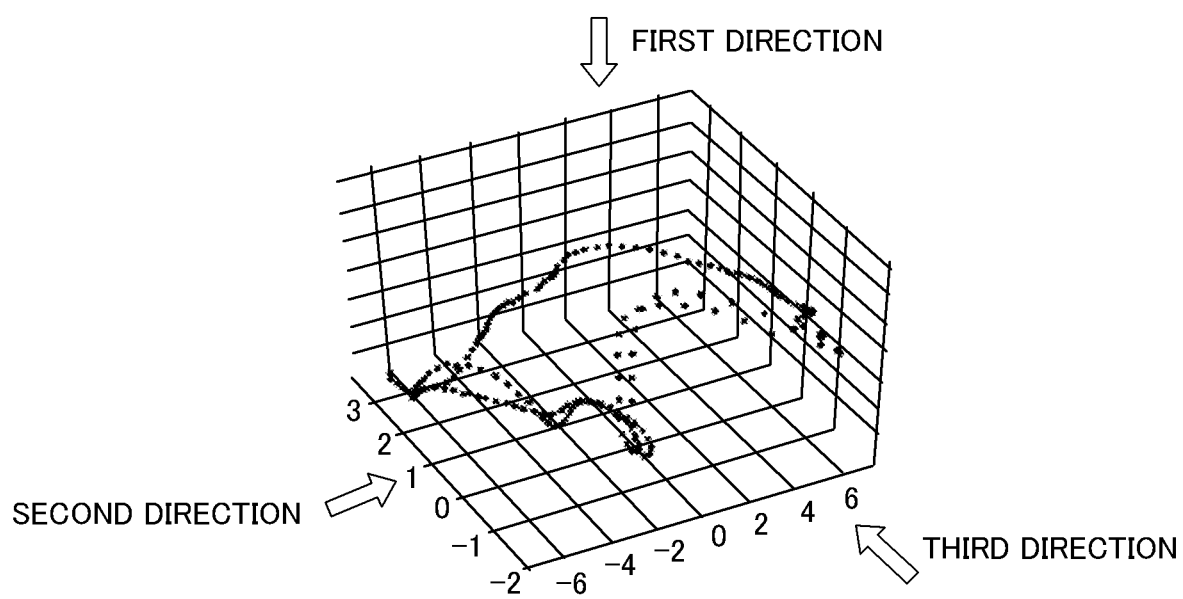
FIG. 11A is a graph showing an example of plotting the detection result of a rotative-type arm-swing form, the result being obtained by the angular speed sensor.
Figure 11B:
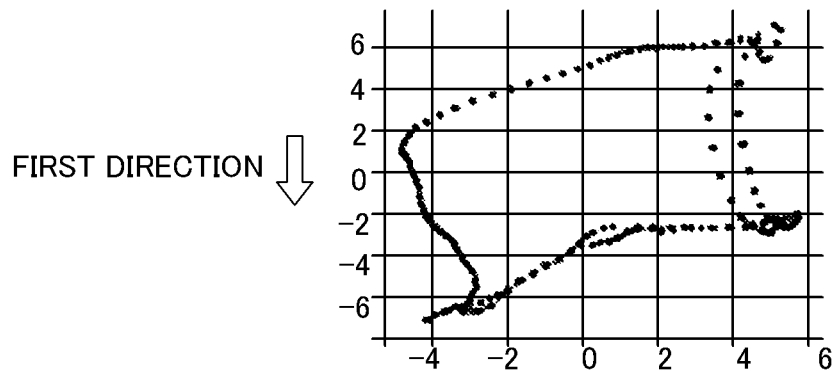
FIG. 11B is a graph showing an example of plotting the detection result of the rotative-type arm-swing form, the result being obtained by the angular speed sensor.
Figure 11C:
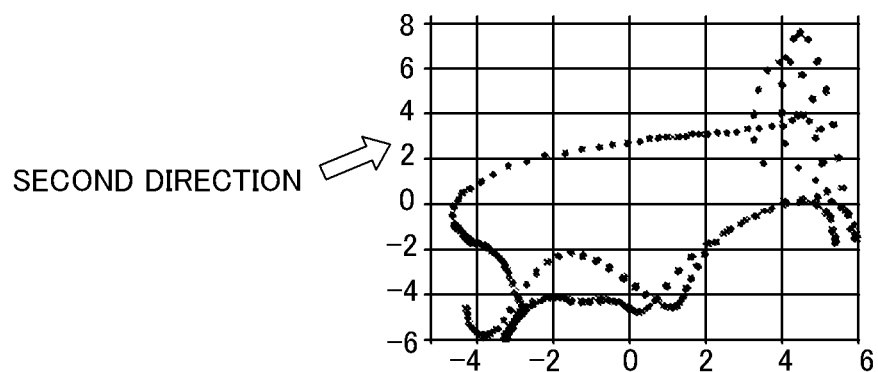
FIG. 11C is a graph showing an example of plotting the detection result of the rotative-type arm-swing form, the result being obtained by the angular speed sensor.
Figure 11D:
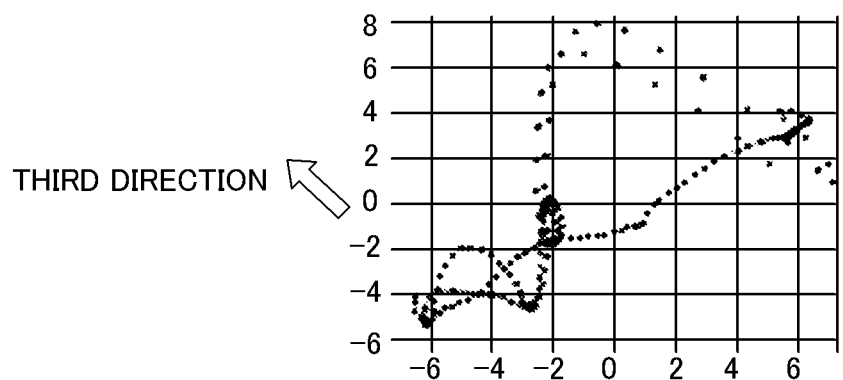
FIG. 11D is a graph showing an example of plotting the detection result of the rotative-type arm-swing form, the result being obtained by the angular speed sensor.

Further, FIG. 11B to FIG. 11D show how much the data disperses (is distributed) in the respective axes when seen from the directions in FIG. 11A (first direction, second direction, third direction in FIG. 11A). FIG. 11B shows the data seen from the first direction. FIG. 11C shows the data seen from the second direction. FIG. 11D shows the data seen from the third direction.

FIG. 10A to FIG. 10D show a case where a person has the straight (two-dimensional) arm-swing form. When the triaxial angular speed data is projected in a three-dimensional space and subjected to the principal component analysis, the resulted scatter (distribution) plot shows a bar shape extending in substantially one direction.

On the other hand, FIG. 11A to FIG. 11D show a case where a person has the rotative (curve) arm-swing form. When the triaxial angular speed data is projected in a three-dimensional space and subjected to the principal component analysis, the resulted scatter (distribution) plot shows such a spread shape that draws a circle.

With regards to the largeness of the arm-swing motion, FIGS. 10A to 10D and FIGS. 11A to 11D are not so different.

In this embodiment, as shown in FIGS. 10A to 10D and FIGS. 11A to 11D, the result of the principal component analysis itself can be an indicator that allows the user US to intuitively recognize the type of his/her arm-swing form.

Therefore, the arm-swing type indicator data to be provided to the user in the following arm-swing type information provision process is not limited to the indicators calculated by the arithmetic circuit 100 using the expressions 1, 2. The arm-swing type indicator data may be the result of the principal component analysis itself, as shown in FIGS. 10A to 10D and FIGS. 11A to 11D (e.g., scatter diagram in each axis).

(Arm-Swing Type Information Provision Process)

Next, the arm-swing type information provision process in this embodiment is described.

Figure 12:
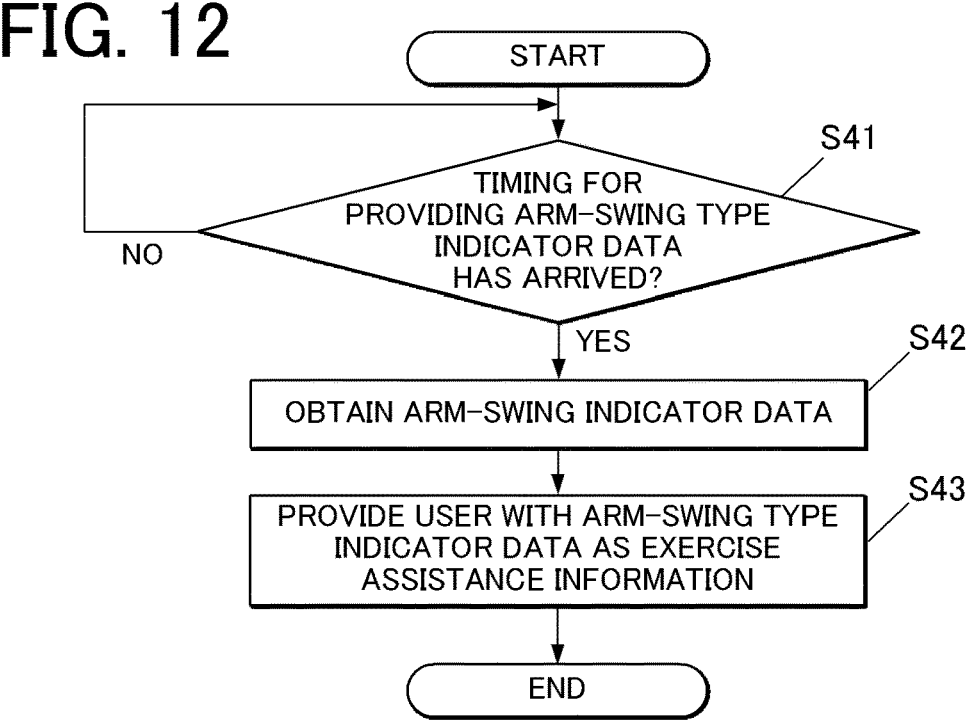
FIG. 12 is a flowchart showing an example of an arm-swing type information provision process in the embodiment.

FIG. 12 is a flowchart showing an example of the arm-swing type information provision process as Step S4 in FIG. 5.

In the arm-swing type information provision process, the arithmetic circuit 100 firstly determines whether a timing for providing the arm-swing type indicator data has arrived (Step S41).

The timing for providing the arm-swing type indicator data is, for example, a timing at which a predetermined amount of the arm-swing type indicator data or more is accumulated.

Herein, "predetermined amount or more" is not limited to a specific amount. For example, the timing may be a timing when 10 data items are accumulated. Alternatively, the information provision process may be performed every time one data item is accumulated.

The timing for providing the information may not be based on the number of accumulated data items. The exercise assistance device 1 may provide information by determining the timing at which a series of running ends or the timing at which the user requires information as the timing for providing the arm-swing type indicator data.

When determining that the timing for providing the arm-swing type indicator data has not yet arrived (Step S41: No) (e.g., a predetermined amount of data or more has not been accumulated or there is no requirement or instruction to provide information), the arithmetic circuit 100 repeats the determination process in Step S41.

When determining that the timing for providing the arm-swing type indicator data has arrived (Step S41: Yes), the arithmetic circuit 100 obtains the arm-swing type indicator data from the memory 101 (Step S42) and provides the user with the arm-swing type indicator data as the exercise assistance information (Step S43).

The method of providing the exercise assistance information is not limited to a specific method.

For example, the display 22 of the exercise assistance device 1 may display the indicator indicating the straightness and the level of rotation of the arm-swing motion and the indicator indicating the largeness of the arm-swing motion, or may display the result of the principal component analysis (e.g., graphs shown in FIGS. 10A to 10D and FIGS. 11A to 11D).

The way of displaying the exercise assistance information is also not limited to a specific way. The exercise assistance information may be displayed three-dimensionally or two-dimensionally. Further, changes in the arm-swing form may be displayed as a moving image. More specifically, the display that shows the result of the principal component analysis and so forth may be chronologically changed. For example, the positions of points in the plot may be changed with passage of time on the basis of the original data. Further, when there are multiple pieces of exercise assistance information, these pieces of information may be displayed as a list in chronological order or may be displayed sequentially with the scrolling operation, for example.

Such a chronological display allows the user to objectively recognize his/her weak points and characteristics. For example, in a case where the arm-swing form starts to break down in the middle of running, the user can recognize how long the user runs until the arm-swing form starts to break down.

Further, the exercise assistance information may be output by the sound outputter 15 outputting a predetermined pattern of sounds, such as a voice or a buzzer. Further, the exercise assistance information may be output by the vibration generator 16 vibrating with a predetermined vibration pattern.

More specifically, when the arm-swing form changes from the straight type to the rotative type during running as an example, the exercise assistance device 1 outputs sounds and/or vibrations indicating that the type of arm-swing form has changed, thereby calling attention of the user US. Further, the exercise assistance device 1 can call attention of the user US by turning on and off the display 22 at the timing when the arm-swing form changes.

Thus, even while the user is running, the exercise assistance device 1 can notify the user US on a real-time basis that the arm-swing form has started to break down with passage of time or owing to accumulated fatigue.

Further, the arithmetic circuit 100 may output the exercise assistance information to an external device that is connected over wired or wireless network via the communication circuit 17. Various terminals, such as a portable terminal (e.g., smartphone) and a personal computer, may then perform display or output sounds on the basis of the exercise assistance information. Further, the arithmetic circuit 100 may output the exercise assistance information via the communication circuit 17 to various wearable devices, such as wireless earphones and augmented reality (AR) glasses (glass-type AR device). In such a case, the user can receive the exercise assistance information during running without stopping to check the portable terminal or the like.

The series of exercise assistance processes then ends.

As described above, according to the embodiment, the exercise assistance device 1 includes: the acceleration sensor 11, the angular speed sensor 12, and the geomagnetic sensor 13 as data obtainers that obtain motion data related to the motion of the arm of the user US that is taking exercise while swinging the arm; and the arithmetic circuit 100 as the arm-swing type obtainer that obtains the arm-swing type of the user on the basis of the motion data obtained by the sensors.

According to such a configuration, a type of arm-swing form can be obtained objectively on the basis of data obtained by the sensors.

The exercise assistance device 1 therefore can provide the arm-swing form during exercise, which is important in running but less noticeable for the user, as the exercise assistance information.

In the embodiment, the exercise assistance device 1 further includes the information provider that provides the user US with the information on the type of arm-swing form of the user US that is obtained by the arithmetic circuit 100 as the arm-swing type obtainer.

More specifically, the exercise assistance device 1 includes: the display 22 capable of displaying the exercise assistance information; and the sound outputter 15 and the vibration generator 16 capable of sending the exercise assistance information to the user by various stimuli, such as sounds and vibrations. Further, the exercise assistance device 1 can output the exercise assistance information to an external device via the communication circuit 17.

The exercise assistance device 1 can notify the user of the information on the type of his/her arm swing form such that the user US can easily understand the information. The exercise assistance device 1 can thereby provide the user with useful information for checking and improving the arm-swing form.

Further, in this embodiment, the arithmetic circuit 100 as an arm-swing type obtainer performs the principal component analysis of the motion data obtained by various sensors as data obtainers (acceleration sensor 11, angular speed sensor 12, and geomagnetic sensor 13) and obtains the type of arm-swing form of the user US on the basis of the level of dispersion of data in respective axis directions.

Accordingly, the exercise assistance device 1 can analyze the type of arm-swing form such that the user can easily understand, and can provide the user with useful exercise assistance information.

Further, in this embodiment, the arithmetic circuit 100 as the arm-swing type obtainer calculates eigenvalues for the respective axis directions in the principal component analysis and, on the basis of the eigenvalues, calculates an indicator indicating the straightness and the level of rotation of the arm-swing form of the user US.

Thus, the exercise assistance device 1 can present the type of arm-swing form of the user US by presenting the indicator indicating the straightness and the level of rotation of the arm-swing form. This allows the user US to objectively recognize the current state of arm-swing form, which is difficult to check by himself/herself.

Further, in this embodiment, the arithmetic circuit 100 as the arm-swing type obtainer calculates eigenvalues for the respective axis directions in the principal component analysis and, on the basis of the eigenvalues, calculates an indicator indicating the largeness of the arm-swing form of the user US.

Thus, the exercise assistance device 1 can present the type of arm-swing form of the user US by presenting the indicator indicating the largeness of the arm-swing form. This allows the user US to objectively recognize the current state of arm-swing form, which is difficult to check by himself/herself.

<Modification>

Although the embodiment of the present invention has been described, the present invention is not limited to the above-described embodiment but can be variously modified without departing from the scope of the invention.

For example, in the embodiment, the exercise assistance device 1 performs the principal component analysis on the basis of motion data (sensor data) obtained mainly by the angular speed sensor 12. The data that is subjected to the principal component analysis is, however, not limited to the motion data obtained by the angular speed sensor 12.

The principal component analysis may be performed on the basis of motion data (sensor data) obtained by the geomagnetic sensor 13, instead of the data obtained by the angular speed sensor 12.

Figure 13A:
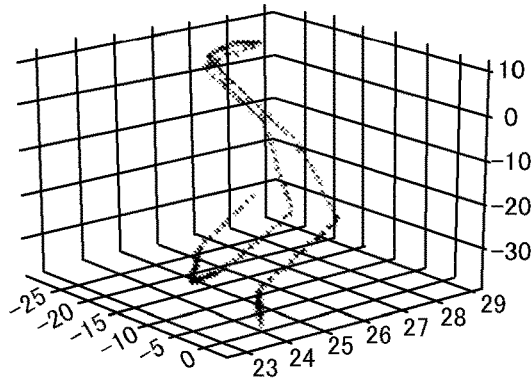
FIG. 13A is a graph showing an example of plotting the detection result of the straight-type arm-swing form, the result being obtained by a geomagnetic sensor.
Figure 13B:
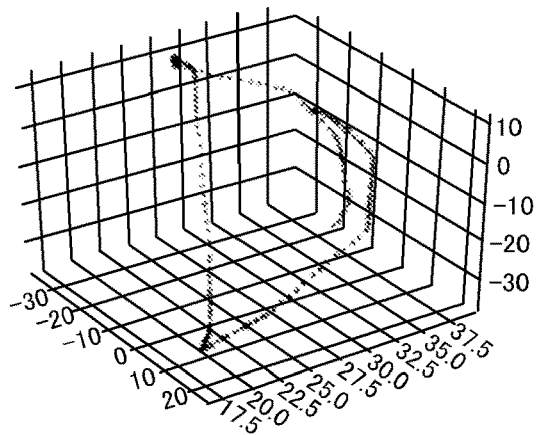
FIG. 13B is a graph showing an example of plotting the detection result of the rotative-type arm-swing form, the result being obtained by the geomagnetic sensor.

FIG. 13A and FIG. 13B show the result of projecting the motion data obtained by the geomagnetic sensor 13 (triaxial geomagnetic data) in a three-dimensional space and performing the principal component analysis of the motion data.

FIG. 13A shows a case where a person has the straight (two-dimensional) arm-swing form. When the triaxial geomagnetic data is projected in a three-dimensional space and subjected to the principal component analysis, the resulted scatter (distribution) plot shows a bar shape extending in substantially one direction.

On the other hand, FIG. 13D shows a case where a person has the rotative (curve) arm-swing form. When the triaxial geomagnetic data is projected on a three-dimensional space and subjected to the principal component analysis, the resulted scatter (distribution) plot shows such a spread shape that draws a circle.

The resulted scatter (distribution) plot is almost the same as that in the case of using the triaxial angular speed sensor 12 (i.e., case shown in FIGS. 10A to 10D and FIGS. 11A to 11D). It can be seen that use of the geomagnetic sensor 13 instead of the angular speed sensor 12 yields the same result.

As described before, the geomagnetic sensor 13 has an advantage of consuming less power than other sensors. Use of the geomagnetic sensor 13 therefore contributes to low energy.

The geomagnetic sensor 13 may be used together with other sensors, such as the angular speed sensor. Obtaining the measurement result using multiple sensors can yield more reliable data.

Further, in the arm-swing type indicator calculation process, the exercise assistance device 1 may detect the running speed of the user US and, on the basis of the running speed, determine how many cycles of motion data are used for the process, for example.

In such a case, an additional sensor that detects the speed of the user US may be attached to the leg/foot or waist of the user, for example.

In the case, the exercise assistance device 1 may change the number of motion data items used in the process according to the change in the speed of the user US.

Further, although the exercise assistance device 1 in the embodiment includes the acceleration sensor 11, the angular speed sensor 12, and the geomagnetic sensor 13, the sensors of the exercise assistance device 1 are not limited to these sensors. Further, the exercise assistance device 1 may not include all of the above sensors.

Other sensors that can be provided to the exercise assistance device 1 are a barometric sensor and a heartbeat sensor, for example.

The barometric sensor uses capacitance, piezoresistance, or a strain gauge, for example. The barometric sensor detects the atmospheric pressure around the exercise assistance device 1. The barometric sensor may be a barometric altitude sensor capable of detecting the altitude on the basis of relationship between atmospheric pressure and altitude.

The heartbeat sensor is a pulse wave sensor that monitors changes of the capacity of blood vessels according to blood pumping by the heart and captures the changes as waveforms.

The barometric sensor and the heartbeat sensor may not be housed in the exercise assistance device 1. The barometric sensor/heartbeat sensor may be separately attached to part of the body of the user US and capable of sending data to the exercise assistance device 1 (and an external device when the exercise assistance device 1 and an external device operate in cooperation with each other).

Further, the exercise assistance device 1 may include global positioning system (GPS) detector capable of detecting GPS information. The exercise assistance device 1 including the GPS detector receives signals from GPS satellites and generates positional information of the exercise assistance device 1. The exercise assistance device 1 including the GPS detector may be capable of appropriately correcting altitude information, which is obtained by a pressure altitude sensor or the like, on the basis of the positional information by GPS. The GPS detector may use signals of navigation satellites other than GPS satellites.

When the exercise assistance device includes the pressure altitude sensor and the GPS detector and is capable of obtaining changes in altitude during running, the changes in altitude may be used as an indicator for estimating the degree of fatigue of the user US. More specifically, when the running road has many upward slopes and it is estimated that the user US is tired, the information on the degree of fatigue may be added to the exercise assistance information in the embodiment.

This allows the user US to recognize that the arm-swing form started to break down in a section where fatigue may accumulate, thereby providing meaningful exercise assistance information.

Further, when the exercise assistance device 1 includes the heartbeat sensor, the exercise assistance device 1 can estimate the degree of fatigue of the user US on the basis of changes in heartbeats. The information on the changes in heartbeats may also be added to the exercise assistance information. This allows the user US to objectively recognize his/her condition and degree of fatigue. The exercise assistance device 1 can provide the user with materials for analyzing how and in what condition the arm-swing form changes as the exercise assistance information, so that the user US can utilize the materials in the training later on.

Further, in the embodiment, the exercise assistance device 1 includes the display 22, the sound outputter 15, and the vibration generator 16 as information providers (outputters) that provide (notify) exercise assistance information to the user US. The exercise support device 1, however, may include only part of these outputters.

The exercise assistance device 1 may include at least either the sound ouputter 15 or the vibration generator 16 in addition to or instead of the display 22.

It is not essential for the exercise assistance device to include the information providers (outputters). For example, the exercise assistance device 1 may only obtain (generate) arm-swing type data (exercise assistance information) of the user US and output the data to any separate external device.

Further, although the exercise assistance device in the embodiment is configured as a single wristwatch-type device, the configuration of the exercise assistance device is not limited to this.

Figure 14:
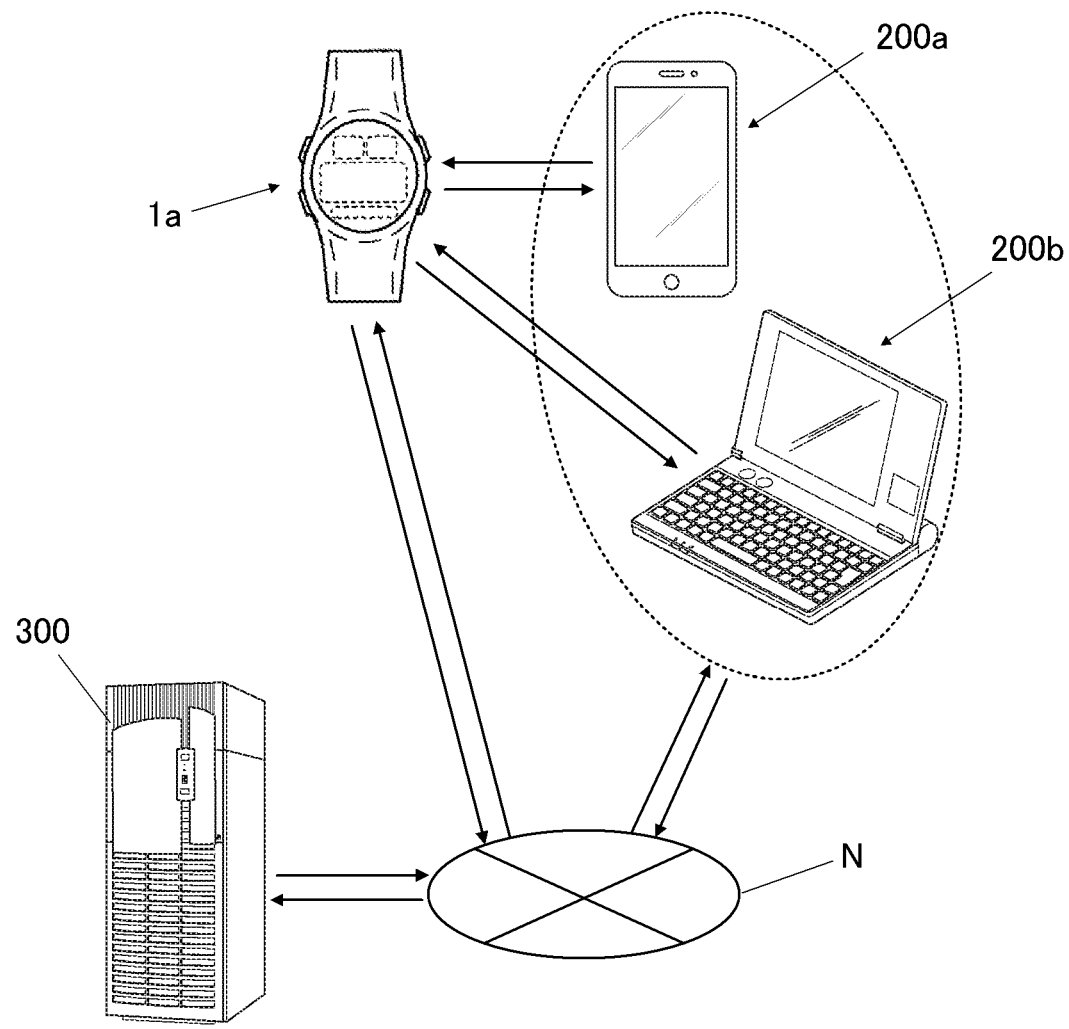
FIG. 14 is a schematic view of the exercise assistance device that is configured as a system in which multiple devices operate in cooperation with each other.

For example, the exercise assistance device may be configured as a system in which a wristwatch-type terminal device 1*a*, which is the same as the exercise assistance device 1 in the embodiment, operates in cooperation with multiple external devices, as shown in FIG. 14.

FIG. 14 shows a case where the wristwatch-type terminal device 1*a* wearable on the wrist of the user and external terminal devices (e.g., portable terminal device 200*a* such as a smartphone, and a terminal device 200*a* such as a personal computer at home) are connected to each other for communication and where the terminal device 1*a* and the external terminal deices 200*a*, 200*b* are connected to a server 300 over a network N. By connecting these devices, the user US can check the exercise assistance information anywhere. Further, the exercise assistance information can be shared among multiple users.

When the exercise assistance device is configured as a system in which multiple devices operate in cooperation with each other, sensors may be distributed to the multiple devices.

Further, a storage that stores an arithmetic circuit and the exercise assistance program in the embodiment may be provided to a device separate from the devices that have sensors.

For example, the motion data (sensor data) obtained by a sensor provided to the wristwatch-type terminal device 1*a* may be sent to the portable terminal device 200*a* (e.g., smartphone) and/or the terminal device 200*b* (e.g., personal computer at home) that include the arithmetic circuit. The portable terminal device 200*a* and/or the terminal device 200*b* may then perform the arm-swing cycle estimation process and the arm-swing type indicator calculation process in the exercise assistance method.

Further, the information providers, such as the sound outputter and the display that performs display for providing information in the arm-swing type information provision process, may be separately provided to multiple devices or may be shared among multiple devices.

Further, the exercise assistance device 1 may obtain the motion data (sensor data), which is output by various sensors (in the embodiment, the acceleration sensor 11, angular speed sensor 12, and geomagnetic sensor 13), from another device(s) outside the exercise assistance device 1. In such a case, the communication circuit 17 of the exercise assistance device 1 receives the motion data (sensor data) from communication units of the external device over any wired/wireless communication method. Herein, the communication circuit 17 of the exercise assistance device 1 serves as a data obtainer.

Although one or more embodiments of the present invention have been described, the scope of the present invention is not limited to the above-described embodiment but includes the scope of claims and the scope of their equivalents.

INDUSTRIAL APPLICABILITY

The present invention is industrially applicable in the field of exercise assistance for assisting users in taking exercise.

The invention claimed is:

1. An exercise assistance device comprising:
a data obtainer that obtains motion data on a motion of an arm of a user that is taking exercise while swinging the arm; and
at least one processor that performs principal component analysis of the motion data obtained by the data obtainer, and obtains, based on a result of performing the principal component analysis, arm-swing type information indicative of a type of arm-swing form of the user, wherein the type of arm-swing form of the user is a type of movement pattern in which the user swings their arm,
wherein:
the data obtainer comprises at least one sensor which detects the motion data in each of a plurality of axis directions,
in obtaining the arm-swing type information, the at least one processor obtains the arm-swing type information based on a level of dispersion of the motion data in each of the axis directions which is obtained by performing the principal component analysis, and
the at least one processor calculates eigenvalues in the respective axis directions, and based on the eigenvalues, the at least one processor calculates an indicator value indicating a straightness and a level of rotation of the arm swing form of the user, as the arm-swing type information.

2. The exercise assistance device according to claim 1, wherein:
based on the eigenvalues, the at least one processor calculates an indicator value indicating a largeness of arm swing in the arm swing form of the user.

3. The exercise assistance device according to claim 1, further comprising an information provider that provides the user with the arm-swing type information obtained by the at least one processor.

4. The exercise assistance device according to claim 1, further comprising:
an output device comprising at least one of a speaker, a display, and a vibrator;
wherein:
the at least one processor obtains the arm-swing type information indicative of the type of arm-swing form of the user in real time while the user is swinging their arm during the exercise, and
the at least one processor detects, in real time based on the obtained arm-swing type information, that the type of arm-swing form has changed during the exercise, and
the at least one processor outputs, via the output device, in real time while the user is swing their arm during the exercise, an alert to the user indicating that the type of arm-swing form has changed.

5. An exercise assistance method that is performed by an exercise assistance device comprising at least one processor and a data obtainer including at least one sensor which detects motion data in each of a plurality of axis directions, the method comprising:
obtaining, by the data obtainer, motion data on a motion of an arm of a user that is taking exercise while swinging the arm, the motion data being detected by the at least one sensor in each of the plurality of axis directions; and performing, by the at least one processor, principal component analysis of the obtained motion data, and obtaining, by the at least one processor, based on a result of performing the principal component analysis, arm-swing type information indicative of a type of arm-swing form of the user, wherein the type of arm-swing form of the user is a type of movement pattern in which the user swings their arm, wherein said obtaining the arm-swing type information comprises obtaining, by the at least one processor, the arm-swing type information based on a level of dispersion of the motion data in each of the axis directions which is obtained by performing the principal component analysis, calculating, by the at least one processor, eigenvalues in the respective axis directions, and calculating, by the at least one processor, based on the eigenvalues, an indicator value indicating a straightness and a level of rotation of the arm swing form of the user, as the arm-swing type information.

6. The exercise assistance method according to claim 5, wherein the exercise assistance device further comprises an output device comprising at least one of a speaker, a display, and a vibrator;

wherein:

the arm-swing type information indicative of the type of arm-swing form of the user is obtained in real time while the user is swinging their arm during the exercise, and the method further comprises:

detecting, by the at least one processor, in real time based on the obtained arm-swing type information, that the type of arm-swing form has changed during the exercise, and outputting, by at least one processor and via the output device, in real time while the user is swinging their arm during the exercise, an alert to the user indicating that the type of arm-swing form has changed.

7. A non-transitory computer-readable storage medium storing a program that is executable by a computer to control the computer to perform functions comprising:

obtaining, from a data obtainer including at least one sensor which detects motion data in each of a plurality of axis directions, motion data on a motion of an arm of a user that is taking exercise while swinging the arm, the motion data being detected by the at least one sensor in each of the plurality of axis directions; and performing principal component analysis of the obtained motion data, and obtaining, based on a result of performing the principal component analysis, arm-swing type information indicative of a type of arm-swing form of the user, wherein the type of arm-swing form of the user is a type of movement pattern in which the user swings their arm, wherein said obtaining the arm-swing type information comprises obtaining the arm-swing type information based on a level of dispersion of the motion data in each of the axis directions which is obtained by performing the principal component analysis, calculating eigenvalues in the respective axis directions, and calculating, based on the eigenvalues, an indicator value indicating a straightness and a level of rotation of the arm swing form of the user, as the arm-swing type information.

8. The non-transitory computer-readable storage medium according to claim 7, wherein:

the arm-swing type information indicative of the type of arm-swing form of the user is obtained in real time while the user is swinging their arm during the exercise, and the program is executable by the computer to control the computer to perform further functions comprising:

detecting, in real time based on the obtained arm-swing type information, that the type of arm-swing form has changed during the exercise, and outputting, via an output device comprising at least one of a speaker, a display, and a vibrator, in real time while the user is swinging their arm during the exercise, an alert to the user indicating that the type of arm-swing form has changed.

* * * * *